United States Patent [19]

Wiley

[11] Patent Number: 4,552,011
[45] Date of Patent: Nov. 12, 1985

[54] ESTABLISHING A DIFFERENTIAL PRESSURE ACROSS A CORE SAMPLE OR CALIBRATING A DIFFERENTIAL PRESSURE TRANSDUCER

[75] Inventor: Bruce F. Wiley, Bartlesville, Okla.

[73] Assignee: Phillips Petroleum Company, Bartlesville, Okla.

[21] Appl. No.: 655,828

[22] Filed: Oct. 1, 1984

Related U.S. Application Data

[60] Division of Ser. No. 427,258, Sep. 29, 1982, Pat. No. 4,487,056, which is a continuation-in-part of Ser. No. 282,307, Jul. 10, 1981, abandoned.

[51] Int. Cl.[4] ............... G01L 27/00; G01N 15/08
[52] U.S. Cl. .............................. 73/4 R; 73/38; 73/703
[58] Field of Search ............ 73/4 R, 38, 153, 703, 73/747, 749

[56] References Cited

U.S. PATENT DOCUMENTS

| | | | |
|---|---|---|---|
| 585,883 | 7/1897 | Bosworth | 73/4 |
| 3,008,332 | 11/1961 | Charbonnier et al. | 73/703 |
| 3,212,338 | 10/1965 | O'Maley | 73/703 |
| 3,262,305 | 7/1966 | Dawley | 73/4 |
| 4,026,156 | 5/1977 | Bowditch et al. | 73/747 |

Primary Examiner—Herbert Goldstein
Attorney, Agent, or Firm—French and Doescher

[57] ABSTRACT

Transmission and reception of sonic waves and the adjustment of the water level in columns are utilized to establish a desired differential pressure across a core sample. The technique utilized to establish a desired differential pressure across a core sample can also be used to calibrate a differential pressure transducer if desired.

14 Claims, 3 Drawing Figures

ESTABLISHING A DIFFERENTIAL PRESSURE ACROSS A CORE SAMPLE OR CALIBRATING A DIFFERENTIAL PRESSURE TRANSDUCER

This application is a division of application Ser. No. 427,258, filed Sept. 29, 1982, now U.S. Pat. No. 4,487,056, which is a continuation-in-part of application Ser. No. 282,307, filed July 10, 1981, now abandoned.

This invention relates to method and apparatus for ascertaining the imbibition characteristics of a rock formation. In one aspect this invention relates to method and apparatus for ascertaining the imbibition characteristics of a rock formation at an elevated temperature and pressure. In another aspect this invention relates to method and apparatus for ascertaining the imbibition characteristics of a rock formation using a core sample which has been restored to its original state of water and gas-oil saturation.

This invention also relates to method and apparatus for measuring a differential pressure across a core sample, where the differential pressure is created by the difference in the height of a liquid in two reservoirs, so that a desired differential pressure can be established across the core sample. This invention also relates to method and apparatus for calibrating a differential pressure transducer.

Optimum recovery of residual oil in a reservoir by water flood methods requires knowledge of the natural tendencies of the reservoir rock to imbibe or absorb those particular waters which are available for the flooding operations. The imbibition characteristics of a reservoir rock can be used to provide a variety of information such as the optimum pressure which should be applied to the reservoir in the water flood operation, the predicted rate at which oil can be produced under specified conditions and other similar information.

In the past, imbibition characteristics of a reservoir rock have generally been determined in a laboratory at relatively low pressures and temperatures using restored state core samples which contain stock tank oil that does not contain any gas. Measurements of the imbibition characteristics of a rock formation under such conditions fails to consider the effect of pore pressure, overburden pressure and temperature of the formation from which the core specimen was derived. Such measurements also fail to consider the effect of the presence of gas in the oil contained in the reservoir. The pore size may change and microscopic cracks will generally occur in the core sample when the sample is removed from the rock formation because of the change in pore pressure, overburden pressure and temperature to which the core sample is subjected. These changes will generally affect the imbibition characteristics of the core sample. Also, the concentration of gas in the oil contained in the reservoir will affect the imbibition characteristics of the reservoir. Therefore, if the in situ imbibition characteristics of the core specimen are desired, then in situ environmental conditions must be included in the imbibition characteristics measurement.

It is thus an object of this invention to provide method and apparatus for ascertaining the imbibition characteristics of a rock formation at elevated temperature and pressures. It is another object of this invention to provide method and apparatus for ascertaining the imbibition characteristics of a rock formation using a core sample which has been restored to its original state of water and gas-oil saturation.

In order to measure the imbibition characteristics of a reservoir rock, it is necessary to establish a desired differential pressure across the core sample. A very small differential pressure is required at operating pressures which are generally on the order of several thousand pounds per square inch (PSI). Differential pressure transducers generally lack the capability to provide repeatable measurements under these conditions and thus the accuracy of the imbibition measurement may suffer if a differential pressure transducer is used to measure the differential pressure across the core sample. It is thus another object of this invention to provide method and apparatus for measuring a differential pressure across a core sample, where the differential pressure is created by the difference in the height of a liquid in two reservoirs, so that a desired differential pressure can be established across the core sample.

In some applications, it is desirable to be able to use a differential pressure transducer where a very small differential pressure is to be measured at high operating pressures even though the repeatability of the measurements may suffer. In order to maximize the accuracy of the measurement of the differential pressure using a differential pressure transducer under such conditions, it is desirable to be able to calibrate the differential pressure transducer at the high operating pressures. It is thus another object of this invention to provide method and apparatus for calibrating a differential pressure transducer which method and apparatus are particularly applicable where the differential pressure to be measured is small but the operating pressure is high.

In accordance with the present invention, method and apparatus is provided for injecting water into a core sample which has been restored to a desired state of water and gas-oil saturation and which is subjected to desired conditions of pore pressure, overburden pressure and temperature. A measurement of the rate at which oil is forced from the core sample by the injected water provides an indication of the imbibition characteristics of the core sample and thus of the rock formation from which the core sample was taken.

In general, the measurement of the imbibition characteristics may be accomplished by first restoring a core sample to its original state of water and oil saturation using connate water and stock tank oil. The core sample is then placed in a pressure cell and the overburden and pore pressures and the temperature are raised to the desired operating levels. Once these desired operating levels have been attained, crude oil with a desired gas-oil ratio is introduced into the core sample to displace substantially all of the stock tank oil. Water, which is preferably the same as the water which would be used in flooding operations, is then introduced into the core sample and measurements of the rate at which oil is removed from the core sample provides an indication of the imbibition characteristics of the core sample and thus of the rock formation from which the core sample was taken.

Also in accordance with the present invention, method and apparatus is provided for measuring a differential pressure based on the travel time of reflected sound waves in the liquid contained in two columns, wherein the differential pressure is created by the difference in the height of the liquid in the two columns. For the imbibition measurement system, two columns are utilized to create a differential pressure across a core sample. The liquid in the two columns is preferably brine. The differential pressure across the core sample can be measured based on the density of the brine and the travel time of a sonic pulse through the brine at operating conditions.

A differential pressure transducer is calibrated in accordance with the present invention by connecting the differential pressure transducer between the two columns previously described. Since the differential pressure between the two columns can be measured based on the travel time of reflected sound waves, the differential pressure seen by the differential pressure transducer will be known and the output from the differential pressure transducer can be calibrated. High pressures can be applied to the columns which provide a means for calibrating a differential pressure transducer at high operating pressures.

Other objects and advantages of the invention will be apparent from the foregoing brief description of the invention and the claims as well as from the detailed description of the drawings in which:

The invention is described in terms of a particular apparatus and in terms of particular method steps. However, the invention is not limited to the particular apparatus utilized to describe the invention and is not limited to the particular method steps which are presently preferred. The invention is applicable to any apparatus and any set of method steps which accomplish the purpose of the present invention. It is particularly noted that other valving systems could be utilized and the flow of fluids could be redirected with respect to the valving system and fluid flow illustrated in FIG. 1.

The invention is also described in terms of measuring the imbibition characteristics of a core sample at pressures, temperature, and water and gas-oil saturation which simulate reservoir conditions. However, the invention is applicable to measuring the imbibition characteristics of a core sample at any elevated temperature and pressure under any conditions of water and gas-oil saturation. Further, the invention is described in terms of using the water which would be utilized in a flooding operation to measure the imbibition characteristics of the core sample. However, any suitable water could be utilized to measure the imbibition characteristics of the core sample.

The portion of the invention directed to the measurement of a differential pressure is described in terms of measuring the differential pressure across a core sample. However, the method and apparatus for measuring a differential pressure are applicable to any system in which a differential pressure can be created by the difference in the height of fluid in two columns.

Figure 1:
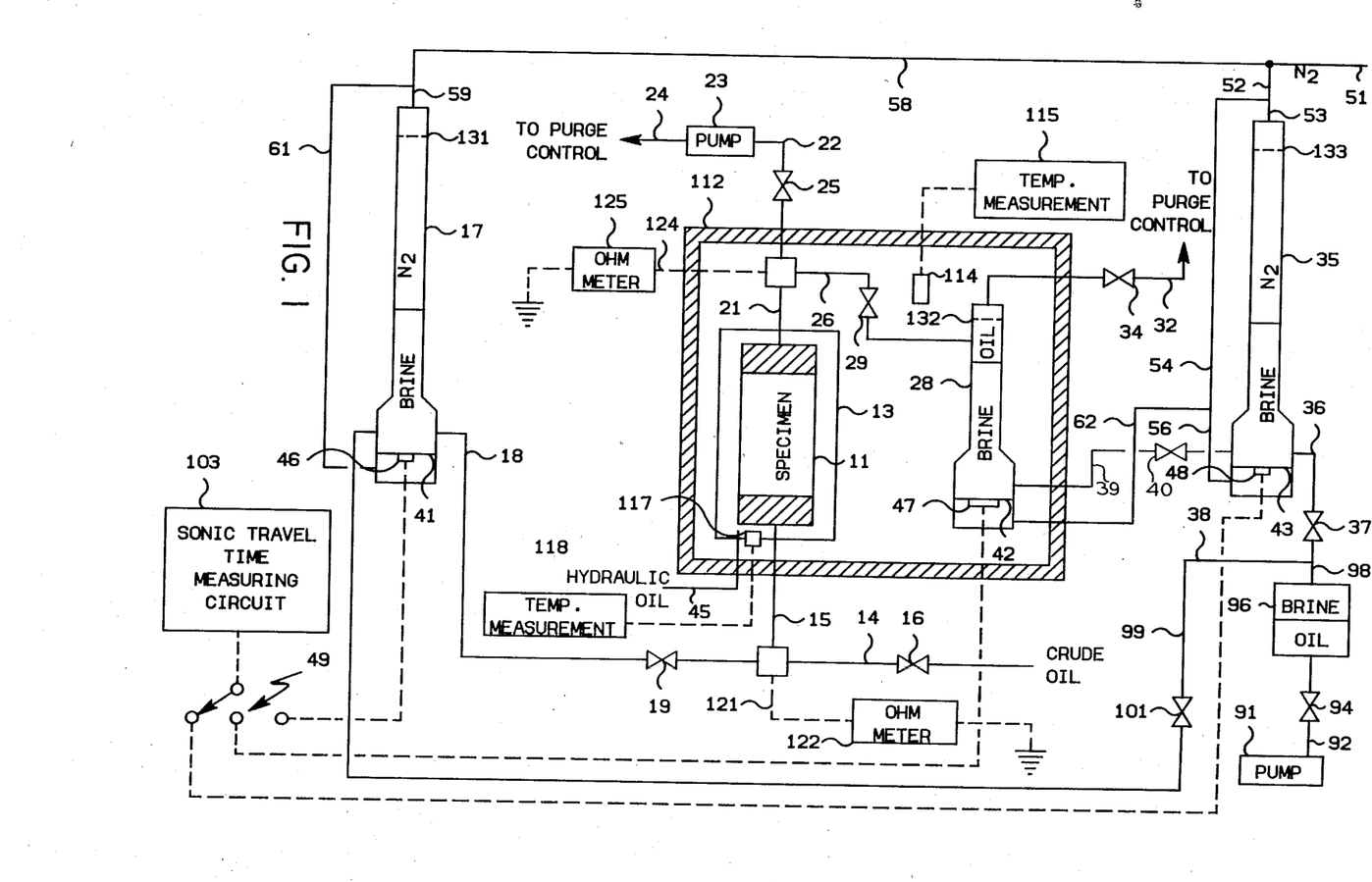
FIG. 1 is a diagrammatic view of the apparatus of the present invention for determining the imbibition characteristics of a core sample under conditions of elevated temperature and pressure.

Referring now to the drawings, and in particular to FIG. 1, a jacketed core sample 11 is contained within the hydrostatic cell 13. Crude oil having a desired gas-oil ratio is provided through the combination of conduit means 14 and 15 to the inlet face of the core sample 11. Control valve 16, which is operably located in conduit means 14, is utilized to manipulate the flow of crude oil to the inlet face of core sample 11. Water is provided from the column 17 through the combination of conduit means 18 and 15 to the inlet face of the core sample 11. Control valve 19, which is operably located in conduit means 18, is utilized to manipulate the flow of water to the inlet face of the core sample 11.

Fluid is withdrawn from the exit face of the core sample 11 through conduit means 21. Depending on the position of the control valves, the thus withdrawn fluid may flow through conduit means 22 to pump 23 and may then be purged through conduit means 24. The position of control valve 25, which is operably located in conduit means 22, determines whether fluid can flow to the pump 23. Alternately, fluid withdrawn through conduit means 21 can flow through conduit means 26, in which control valve 29 is operably located, to the collector column 28. Oil flowing through conduit means 26 exits through a small orifice (1/16" actually used) at the end of conduit means 26 into the oil collected at the top of the collector column 28. Fluid in the collector column 28 can be withdrawn through conduit means 32 in which control valve 34 is operably located.

The collector column 28 is in fluid communication with column 35 through conduit means 39. Control valve 37 is operably located in conduit means 36 and control valve 40 is operably located in conduit means 39. These control valves provide the means by which the flow of fluid between the column 35 and the collector column 28 can be manipulated.

Each of the columns 17, 28 and 35 contains a thin metal diaphragm 41-43 respectively. The thickness used in actual practice was 0.003 inches. A lead zirconium titanate (PZT) transducer 46-48 is cemented to the lower side of the metal diaphragms 41-43 respectively. The transducer element actually used was ¼ inch in diameter and ⅛ inch thick. Such a transducer transmits in the ultrasonic range.

The metal diaphragms 41-43 serve to acoustically couple the PZT transducers 46-48 to the liquid in the columns 17, 28 and 35 respectively. The diaphragms also electrically isolate the PZT transducers from the brine. The PZT transducers 46-48 are electrically connected to the switch 49.

Nitrogen under pressure is provided through the combination of conduit means 51, 52 and 53 to the upper portion of the column 35 and is also provided through combination of conduit means 51, 52, 54 and 56 to the lower portion of the column 35 which is below the diaphragm 43. In like manner, nitrogen under pressure is provided through the combination of conduit means 51, 58 and 59 to the upper portion of the column 17 and through the combination of conduit means 51, 58 and 61 to the lower portion of the column 17 which is below the diaphragm 41. Nitrogen under pressure is also provided through the combination of conduit means 51, 52, 54 and 62 to the lower portion of the oil-water separator 28 which is below the diaphragm 42.

It is noted that since the pressure above the diaphragms 41-43 will be essentially the same as the pressure below the diaphragms 41-43, the only loading on the diaphragms is due to the hydrostatic head of liquid in the columns and no undue stress is placed on the diaphragms regardless of system pressure levels. Also, since the fluid on the top side of the diaphragms is a liquid and the fluid on the back or underside is a gas, ideal acoustic coupling in the direction of the liquid is achieved and unwanted reflections from the backside are minimized.

A Ruska pump 91 is utilized to control the level of the brine in the columns 17, 28 and 35. Oil is pumped from the pump 91 through conduit means 92, in which control valve 94 is operably located, to the tank 96 which contains oil and brine. Brine is pumped from the tank 96 through the combination of conduit means 98 and 36 to column 35, from column 35 through conduit means 39 to column 28 and through the combination of conduit means 98, 38, and 99, in which control valve 101 is operably located, to column 17.

The sonic wave travel time measuring system described in U.S. Pat. No. 4,300,394 may be utilized as the sonic travel time measuring circuit 103. Only one of the monostable multivibrators 34 and 35 illustrated in FIG. 1 of U.S. Pat. No. 4,300,394 is needed because there is not a necessity for two different delays. The receiver/pulser 25 illustrated in FIG. 1 of U.S. Pat. No. 4,300,394 is preferably a Panametrics Pulser/Receiver, Model 505PR which has the capability of both transmitting and receiving from the same terminal. Thus, each of the PZT transducers 46–48 can be wired by a single wire and ground through the switch 49 to a single input of the receiver/pulser illustrated in FIG. 1 of U.S. Pat. No. 4,300,394.

Because a single input of the receiver/pulser is being utilized, a delay is preferably introduced by means of a monostable multivibrator to prevent the transmission from triggering the receiver to stop the clock because of a feedback or ringing effect. In the present case, a delay of 200μ sec was used. Thus, any received acoustic pulses are ignored for 200μ sec which effectively prevents the transmission from stopping the clock. The reflected wave stops the clock.

Hydraulic oil under pressure is provided to the hydrostatic cell 13 through conduit means 45. The hydraulic oil is utilized to provide a desired overburden pressure for the core sample 11.

Both the hydrostatic cell 13 and the collector 28 are contained in an oven 112. A temperature measuring device such as a thermocouple 114 provides an indication of the temperature in the oven 112 to a temperature indicating device 115 which may be a digitial thermometer. In like manner, a temperature sensing device such as the thermocouple 117 provides an indication of the temperature in the hydrostatic cell 13 to a temperature indicating device 118 which also may be a digital thermometer.

An insulated wire 121 having one end electrically connected to a grounded ohm meter 122 extends through conduit means 15 to the fluid entrance face of the core sample 11. The end of the insulated wire 121 is bare at the entrance face of the core sample 11. When water flowing through conduit means 18 reaches the bare end of the wire 121, the bare end of the wire 121 will be grounded and a substantially zero resistance will be seen by the ohm meter 122. In this manner, an indication is provided of the time when the water flowing through conduit means 18 reaches the entrance face of the core sample 11. The wire 124, which is electrically connected to the grounded ohm meter 125, extends through conduit means 21 to the exit face of the core sample 11 and performs a function similar to the function performed by the wire 121. The bare end of the wire 124 will be grounded when water reaches the exit face of the core sample 11 and thus an indication is provided of the break through of the water through the core sample 11.

A typical sequence for ascertaining the imbibition characteristics of a core sample using the apparatus illustrated in FIG. 1 is as follows.

A core sample from a rock formation is first restored to its original state of water and oil saturation using connate water and stock tank oil. The thus prepared core sample is then placed in the hydrostatic cell 13.

Brine is introduced into the columns 17, 28 and 35 by opening control valve 94 and control valves 37, 40 and 101. Control valves 37, 40 and 101 can be opened simultaneously or in a desired sequence. Brine is added to the columns 17, 28 and 35 until the fluid level in each column is above the level of the reflector plates 131–133. During the time in which brine is being added to the columns, control valves 16, 19, 25 and 29 will be closed while control valve 34 will be opened. After the system is fluid full, control valve 34 will be closed.

It is desirable to have all conduits fluid full. Sometimes it is necessary to open a fitting associated with a control valve to allow fluid to fill a particular conduit. As an example, a fitting on control valve 19 can be opened to allow fluid to fill conduit means 18. Control valves 16 and 25 can be opened to allow crude oil to fill conduit means 14, 15, 21 and 26.

An overburden pressure is applied by means of the hydraulic oil flowing through conduit means 45 to the core sample 11. The overburden pressure is preferably maintained about 1000 psig greater than the pressure applied by means of the nitrogen to the columns 17, 28 and 35. Typical operating pressures are a pore pressure of about 6200 psig and an overburden pressure of about 7200 psig. The overburden pressure should be applied before any fluid under pressure is allowed to flow through the core specimen to avoid rupturing of the jacket surrounding the core specimen 11.

While the pressures on the core sample 11 are being raised to a desired level (both overburden and pore pressure), the oven temperature is increased to a desired temperature and the system is allowed to stabilize in such a manner that the core sample 11 will be at a desired temperature and a desired overburden pressure. Also, a desired nitrogen pressure will have been reached.

After all conduits are fluid full and operating pressures and temperature have been reached, the liquid level measuring system is calibrated by reflecting sonic waves off of the reflector plates 131–133 respectively and observing round trip travel time of the ultrasonic wave. Since the distance between the PZT transducers 46–48 and the reflector plates 131–133 will be known, a correlation can be obtained between the actual sonic travel time and the distance. Thus, when the brine level is allowed to drop below the level of the reflector plates 131–133, the sonic reflections from the brine-nitrogen interface provides an extremely accurate measurement of the height of the brine. This measurement, taken together with a knowledge of the density of the brine, is utilized to determine the differential pressure across the core specimen. Tables are available which give the pressure exerted per square inch by a column of brine based on the density of the brine and the height of the brine. The pressure exerted by the brine in column 35 is subtracted from the pressure exerted by the brine in column 17 to give the differential pressure across the core sample 11. Also, the height of the brine in the collector column 28 provides an accurate indication of the amount of oil which has been displaced from the core specimen 11 since the cross-sectional area of column 28 is known.

After the system has been calibrated, the level of the brine in columns 17, and 35 is reduced to a desired level by manipulating the pump 91. The desired level in columns 17 and 35 is determined by the desired differential pressure across the core specimen 11. Column 28 remains full of water.

After a desired differential pressure has been established across the core specimen 11, control valves 37, 94 and 101 are closed and control valves 19, 34 and 35 remain closed. Control valves 16 and 29 are opened while control valve 40 remains open. Crude oil having a desired gas concentration (live crude oil), which is preferably the concentration of gas found in crude oil in the reservoir from which the core sample was taken, is provided through conduit means 14 at a pressure slightly greater than the nitrogen pressure. The crude oil flowing through conduit means 14 displaces substantially all stock tank oil between the entrance face of the core sample 11 and the nozzle exit of conduit means 26. The stock tank oil thus removed is purged through conduit means 32 and valve 34.

After the live crude oil flowing through conduit means 14 has reached the nozzle of conduit means 26, control valves 16, 29 and 34 are closed and control valves 19 and 25 are opened. The pump 23 is utilized to withdraw fluid from the core sample 11 until the water flowing through conduit means 18 reaches the entrance face of the core sample 11 as indicated by the bare end of the wire 121. At this point, control valve 25 is closed. The level of the brine in column 17 and 35 is then adjusted to again provide a desired differential pressure across the core specimen 11 while the level of the brine in the collector column 28 is checked to make sure that sufficient volume is available to measure the volume of oil in the core specimen 11 without forcing all water from the collector colums 28. Data acquisition is then begun.

To acquire data regarding the imbibition characteristics of a core sample, control valve 29 is opened while control valves 19 and 40 remain open. The pressure differential across the core sample 11 will be determined solely by the difference, if any, in the height of the brine in columns 17 and 35. Generally, the pressure differential will be small and will range from about −14 kPa to about +14 kPa depending on the particular characteristics of the core sample and the affinity of the core sample for water. It is noted that the differential pressure across the core sample 11 may be manipulated so as to be greater than zero, zero or less than zero depending upon the relative positions of the brine level in columns 17 and 35. Because of the affinity of many core samples for water, a positive pressure differential across the core sample is often not required to induce water flow from the entrance face to the exit face.

As water enters the core sample 11, crude oil is forced from the core sample 11 and since conduit means 21 and 26 will be full of crude oil, crude oil will be forced into the collector 28. This will cause a change in the level of the brine in the collector 28 which change will be noted by periodically measuring the level by reflecting sonic waves off the oil-brine interface. This system may be calibrated to determine how much oil has entered the collector 28 for any given change in the level of the brine in the collector 28 since the cross-sectional area of the collector 28 is known and thus a very accurate measurement is provided of the oil forced from the specimen 11 as a function of time by periodically measuring the brine level in the collector 28. A measurement of the volume of oil removed from the core sample per unit time provides an indication of the imbibition characteristics of the core sample.

Figure 2:
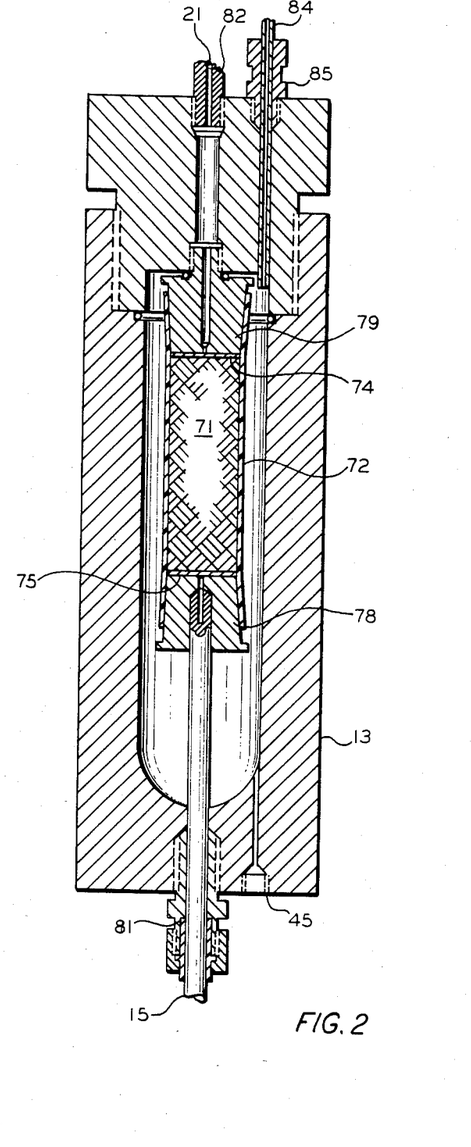
FIG. 2 is a detailed diagrammatic illustration of the apparatus utilized to hold the core sample and to introduce fluid into the core sample.

The hydrostatic cell 13 which contains the jacketed core sample 11 is more fully illustrated in FIG. 2. Referring now to FIG. 2, the core sample 71 is preferably surrounded by a thin, teflon sleeve 72 which preferably has an inside diameter of one inch. The teflon sleeve 72 preferably extends one inch past both ends of the core sample 71. Fritted glass plates 74 and 75, which have an affinity for water, are placed against each end of the core sample 71. End plugs 78 and 79 are utilized to hold the core samples 71 and the fritted glass plates 74 and 75 in place. Conduit means 15 extends through the packing gland 81 to the fritted glass plate 75. Conduit means 21 extends through the pressure fitting 82 to the fritted glass plate 74. The thermocouple 117 illustrated in FIG. 1 is inserted into the thermocouple well 84 which is operably connected to the hydrostatic cell 13 by means of a pressure fitting 85. Conduit means 45 extends into the hydrostatic cell 13 as is illustrated in FIG. 2.

In operation, fluid flows through conduit means 15 and the fritted glass plate 75 into the core sample 71. After passing through the core sample 71, the fluid flows out of the fritted glass plate 74 and through conduit means 21. Overburden pressure is provided to the core sample 71 by means of pressure applied through conduit means 45 as has been previously stated.

Figure 3:
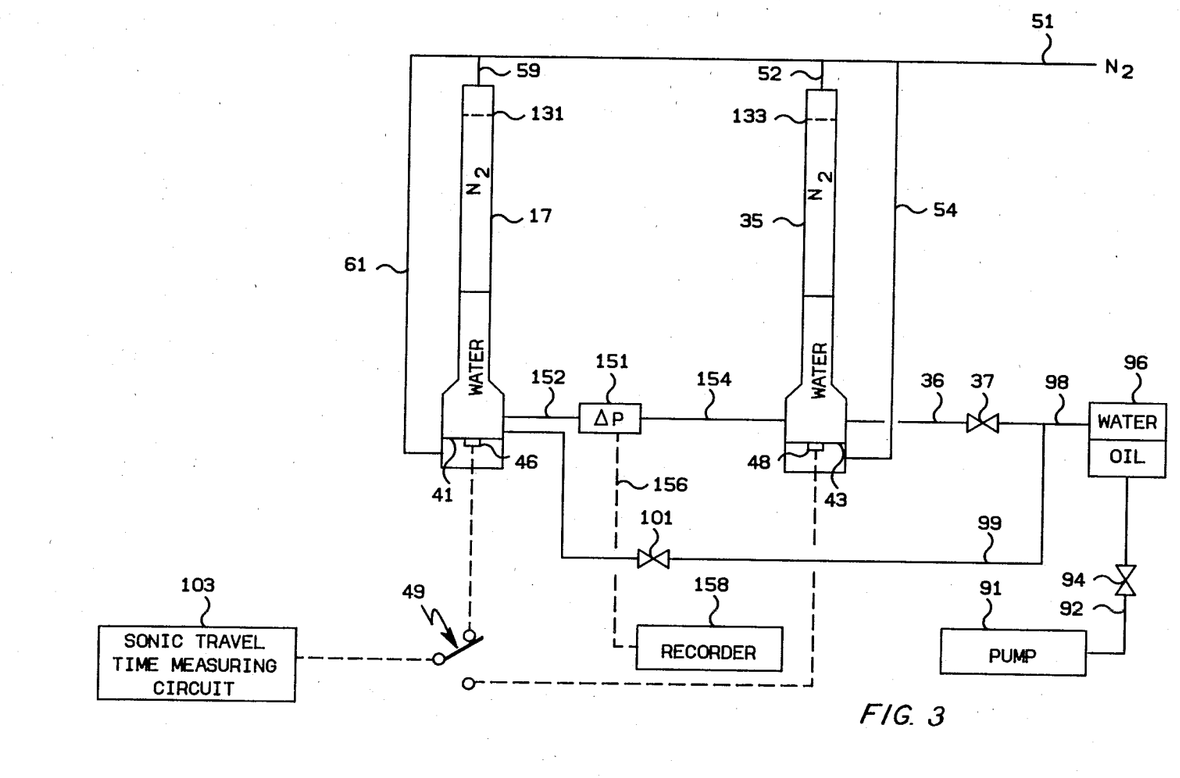
FIG. 3 is a diagrammatic view of the apparatus of the present invention for calibrating a differential pressure transducer.

Referring now to FIG. 3, there is illustrated apparatus by which the apparatus described in FIG. 1 to establish a desired differential pressure can be utilized to calibrate a differential pressure transducer under operating conditions. Apparatus in FIG. 3 which has similar reference numerals to apparatus in FIG. 1 operate in the manner described in FIG. 1. Thus, the illustrated apparatus is utilized to establish a desired differential pressure by establishing a desired difference in the heights of the level of the liquid (water could be used) in the columns 17 and 35. This differential pressure could be established at high nitrogen pressures as was in the case in the apparatus described in FIG. 1 or at no pressure, if desired. Also, the system could be enclosed in an oven if high temperatures were desired.

One side of the diaphragm of the differential pressure transducer 151 is in fluid communication with the liquid in column 17 though conduit means 152. The opposite side of the diaphragm of the differential pressure transducer 151 is in fluid communication with the liquid in column 35 through conduit means 154. The output signal 156 from the differential pressure transducer 151 is provided to the recorder 158.

In operation, a desired differential pressure is set up by changing the level of the liquid in columns 17 and 35. The output from the differential pressure transducer 151 is then observed. Typically, a number of different differential pressures would be measured and the results of these measurements would be utilized to calibrate the differential pressure transducer 151.

Again, this calibration technique is particularly useful when a small differential pressure is to be measured by a differential pressure transducer at high operating pressures. However, the method could be utilized to calibrate the differential pressure transducer for any conditions.

The invention has been described in terms of its presently preferred embodiment as is illustrated in FIGS. 1, That which is claimed is:

1. A method for establishing a desired differential pressure across a core sample, having first and second faces, wherein said first face of said core sample is in fluid communication with a first column containing a gas and water, wherein said second face of said core sample is in fluid communication with a second column containing a gas and water, wherein said water in said first column is supported by a first diaphragm to which a first sonic transducer is attached on the side of said first diaphragm opposite the water and wherein the water in said second column is supported by a second diaphragm to which a second sonic transducer is attached on the side of said second diaphragm opposite the water, said method comprising the steps of:

actuating said first sonic transducer to transmit a first sonic wave through the water contained in said first column, wherein said first sonic wave is reflected from the water-gas interface in said first column;

measuring the time which elapses between the transmission of said first sonic wave and the reception of the reflected first sonic wave by said first sonic transducer, wherein the elapsed time provides a measurement of the height of the water in said first column;

actuating said second sonic transducer to transmit a second sonic wave through the water contained in said second column, wherein said second sonic wave is reflected from the water-gas interface in said second column;

measuring the time which elapses between the transmission of said second sonic wave and the reception of the reflected second sonic wave by said second sonic transducer, wherein the elapsed time provides a measurement of the height of the water in said second column;

determining the pressure exerted by the water contained in said first column based on the density of the water and the height of the water in said first column;

determining the pressure exerted by the water contained in said second column based on the density of the water and the height of the water contained in said second column, wherein the differential pressure across said core sample is the difference in the pressure exerted by the water contained in said first column and the pressure exerted by the water contained in said second column; and adjusting the level of the water contained in said first column and said second column until a desired differential pressure is obtained across said core sample.

2. A method in accordance with claim 1 additionally comprising the steps of:

supplying a gas to said first column on the side of said first diaphragm opposite the water, and;

supplying a gas to said second column on the side of said second diaphragm opposite the water.

3. A method in accordance with claim 1 wherein the differential pressure across said core sample is in the range of about −14 kPa to about +14 kPa.

4. Apparatus comprising:

a hydrostatic cell containing a core sample which has first and second faces;

a first column containing a gas and water which is in fluid communication with said first face of said core sample, wherein said water in said first column is supported by a first diaphragm to which a first sonic transducer is attached on the side of said first diaphragm opposite the water;

a second column containing gas and water which is in fluid communication with the second face of said core sample, wherein the water in said second column is supported by a second diaphragm to which a second sonic transducer is attached on the side of said second diaphragm opposite the water;

means for actuating said first sonic transducer to transmit a first sonic wave through the water contained in said first column, wherein said first sonic wave is reflected from the water-gas interface in said first column;

means for measuring the time which elapses between the transmission of said first sonic wave and the reception of the reflected first sonic wave by said first sonic transducer, wherein the elapsed time provides a measurement of the height of the water in said first column, and wherein the pressure exerted by the water contained in said first column is determined based on the density of the water and the height of the water in said first column;

means for actuating said second sonic transducer to transmit a second sonic wave through the water contained in said second column, wherein said second sonic wave is reflected from the water-gas interface in said second column;

means for measuring the time which elapses between the transmission of said second sonic wave and the reception of the reflected second sonic wave by said second sonic transducer, wherein the elapsed time provides a measurement of the height of the water in said second column, wherein the pressure exerted by the water contained in said second column is determined based on the density of the water and the height of the water contained in said second column and wherein the differential pressure across said core sample is the difference in the pressure exerted by the water contained in said first column and the pressure exerted by the water contained in said second column; and means for adjusting the level of the water contained in said first column and said second column until a desired differential pressure is obtained across said core sample.

5. Apparatus in accordance with claim 4 additionally comprising means for supplying a gas to the side of said first diaphragm opposite the water and to the side of said second diaphragm opposite the water.

6. Apparatus in accordance with claim 4 wherein the differential pressure across said core sample is in the range of about −14 kPa to about +14 kPa.

7. A method for calibrating a differential pressure transducer, having first and second pressure inlets, wherein said first pressure inlet of said differential pressure transducer is in fluid communication with a first column containing a gas and liquid, wherein said second pressure inlet of said differential pressure transducer is in fluid communication with a second column containing a gas and liquid, wherein said liquid in said first column is supported by a first diaphragm to which a first sonic transducer is attached on the side of said first diaphragm opposite the liquid and wherein the liquid in said second column is supported by a second diaphragm to which a second sonic transducer is attached on the side of said second diaphragm opposite the liquid, said method comprising the steps of:

actuating said first sonic transducer to transmit a first sonic wave through the liquid contained in said first column, wherein said first sonic wave is reflected from the liquid-gas interface in said first column;

measuring the time which elapses between the transmission of said first sonic wave and the reception of the reflected first sonic wave by said first sonic transducer, wherein the elapsed time provides a measurement of the height of the liquid in said first column;

actuating said second sonic transducer to transmit a second sonic wave through the liquid contained in said second column, wherein said second sonic wave is reflected from the liquid-gas interface in said second column;

measuring the time which elapses between the transmission of said second sonic wave and the reception of the reflected second sonic wave by said second sonic transducer, wherein the elapsed time provides a measurement of the height of the liquid in said second column;

determining the pressure exerted by the liquid contained in said first column based on the density of the liquid and the height of the liquid in said first column;

determining the pressure exerted by the liquid contained in said second column based on the density of the liquid and the height of the liquid contained in said second column, wherein the differential pressure across said differential pressure transducer is the difference in the pressure exerted by the liquid contained in said first column and the pressure exerted by the liquid contained in said second column;

adjusting the level of the liquid contained in said first column and said second column until a desired differential pressure is obtained across said differential pressure transducer; and comparing the differential pressure represented by the output signal from said differential pressure transducer to the actual differential pressure established by adjusting the level of the liquid contained in said first column and said second column to thereby calibrate said differential pressure transducer.

8. A method in accordance with claim 7 wherein a plurality of known differential pressures are established across said differential pressure transducer by varying the level of the liquid contained in said first column and said second column and wherein the output from said differential pressure transducer for each different differential pressure is compared to the actual differential pressure to calibrate said differential pressure transducer.

9. A method in accordance with claim 7 additionally comprising the step of applying a desired pressure to the gas in said first column and said second column.

10. A method in accordance with claim 9 additionally comprising the steps of:

supplying a gas under said desired pressure to said first column on the side of said first diaphragm opposite the liquid; and supplying a gas under said desired pressure to said second column on the side of said second diaphragm opposite the liquid, wherein the only pressure on said first diaphragm is the pressure exerted by the liquid in said first column and wherein the only pressure on said second diaphragm is produced by the liquid in said second column.

11. Apparatus comprising:

a differential pressure transducer which has first and second pressure inlets;

a first column containing a gas and liquid which is in fluid communication with said first pressure inlet of said differential pressure transducer, wherein said liquid in said first column is supported by a first diaphragm to which a first sonic transducer is attached on the side of said first diaphragm opposite the liquid;

a second column containing a gas and liquid which is in fluid communication with the second pressure inlet of said differential pressure transducer, wherein the liquid in said second column is supported by a second diaphragm to which a second sonic transducer is attached on the side of said second diaphragm opposite the liquid;

means for actuating said first sonic transducer to transmit a first sonic wave through the liquid contained in said first column, wherein said first sonic wave is reflected from the liquid-gas interface in said first column;

means for measuring the time which elapses between the transmission of said first sonic wave and the reception of the reflected first sonic wave by said first sonic transducer, wherein the elapsed time provides a measurement of the height of the liquid in said first column, and wherein the pressure exerted by the liquid contained in said first column is determined based on the density of the liquid and the height of the liquid in said first column;

means for actuating said second sonic transducer to transmit a second sonic wave through the liquid contained in said second column, wherein said second sonic wave is reflected from the liquid-gas interface in said second column;

means for measuring the time which elapses between the transmission of said second sonic wave and the reception of the reflected second sonic wave by said second sonic transducer, wherein the elapsed time provides a measurement of the height of the liquid in said second column, wherein the pressure exerted by the liquid contained in said second column is determined based on the density of the liquid and the height of the liquid contained in said second column and wherein the differential pressure across said differential pressure transducer is the difference in the pressure exerted by the liquid contained in said first column and the pressure exezted by the liquid contained in said second column; and means for adjusting the level of the liquid contained in said first column and said second column until a desired differential pressure is obtained across said differential pressure transducer, wherein the differential pressure represented by the output signal from said differential pressure transducer is compared to the actual differential pressure established by adjusting the level of the liquid contained in said first column and said second column to thereby calibrate said differential pressure transducer.

12. Apparatus in accordance with claim 11 wherein a plurality of known differential pressures are established across said differential pressure transducer by varying the level of the liquid contained in said first column and said second column and wherein the output from said differential pressure transducer for each different differential pressure is compared to the actual differential pressure to calibrate said differential pressure transducer.

13. Apparatus in accordance with claim 11 additionally comprising means for applying a desired pressure to the gas in said first column and said second column.

14. Apparatus in accordance with claim 13 additionally comprising:
means for supplying a gas under said desired pressure to said first column on the side of said first diaphragm opposite the liquid; and
means for supplying a gas under said desired pressure to said second column on the side of said second diaphragm opposite the water, wherein the only pressure on said first diaphragm is the pressure exerted by the liquid in said first column and wherein the only pressure on said second diaphragm is produced by the liquid in said second column.

* * * * *